United States Patent [19]

Dietz et al.

[11] Patent Number: 5,055,580

[45] Date of Patent: Oct. 8, 1991

[54] SUBSTITUTED POLYCYLIC DERIVATIVES OF THE 9-OXO-1,9A,10-TRIAZA-9-HYDROANTHRACENE AND METHOD FOR COLORING OF NATIVE OR SYNTHETIC MATERIALS

[75] Inventors: Erwin Dietz, Kelkheim; Frank Prokschy, Frankfurt am Main, both of Fed. Rep. of Germany

[73] Assignee: Hoechst Aktiengesellschaft, Frankfurt, Fed. Rep. of Germany

[21] Appl. No.: 344,218

[22] Filed: Apr. 27, 1989

[30] Foreign Application Priority Data

Apr. 29, 1988 [DE] Fed. Rep. of Germany ....... 3814552

[51] Int. Cl.[5] ..................... C09B 57/00; C09B 67/22; C09B 67/48; D06P 1/44
[52] U.S. Cl. ................... 544/233; 544/234; 544/287; 106/494
[58] Field of Search ........... 544/234, 235, 233

[56] References Cited

U.S. PATENT DOCUMENTS

| 4,250,177 | 2/1981 | Schwender et al. ............. 544/234 X |
| 4,256,483 | 3/1981 | Asao et al. ...................... 544/234 X |
| 4,716,159 | 12/1987 | Toja ................................ 544/534 X |
| 4,881,980 | 11/1989 | Dietz et al. ..................... 546/49 X |

FOREIGN PATENT DOCUMENTS 3639465  5/1988  Fed. Rep. of Germany ...... 534/235

OTHER PUBLICATIONS

A. Marracini et al., *Dyes and Pigments* 7, 23–32 (1986).

Primary Examiner—Mary C. Lee
Assistant Examiner—Fiona T. Powers

[57] ABSTRACT

Derivatives of 9-oxo-1,9a,10-triaza-9-hydroanthracene of the general formula I

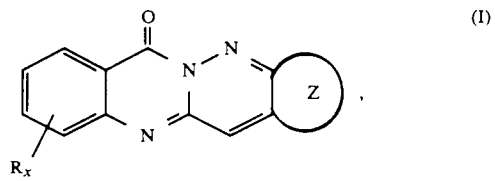

with the exception of three compounds in which R denotes a hydrogen atom, halogen atom, an alkyl-$C_1$-$C_4$, alkoxy-$C_1$-$C_4$ or denotes a trihalogenomethyl group, a —CO—$NH_2$, —CO—NH—(alkyl-$C_1$-$C_4$) or —CO—N(alkyl-$C_1$-$C_4$)$_2$ group or phenyl, alkyl-$C_1$-$C_4$, —$NH_2$, —NH(alkyl-$C_1$-$C_4$), —N(alkyl-$C_1$-$C_4$)$_2$ or an alkylene-$C_1$-$C_4$—$OSO_3H$ group, bound via the bridge member —S—, —SO—or —$SO_2$—, a or a fused-on 4- to 7-membered isocycle or heterocycle, which itself can be part of a polycyclic system, from the series consisting of naphthalene, acenaphthene, phenanthrene and indole, x denotes an integer from 1 to 4, where for x > 1 R can be identical or different, and z denotes a fused-on 4- to 7-membered isocycle or heterocycle, which itself can be part of a polycyclic system, from the series consisting of naphthalene, acenaphthene, phenanthrene and indole, in which each of the 4- to 7-membered isocycles or heterocycles and each of the polycyclic systems mentioned can be substituted, processes for their preparation and their use for the coloring of natural or synthetic materials.

3 Claims, No Drawings

SUBSTITUTED POLYCYLIC DERIVATIVES OF THE 9-OXO-1,9A,10-TRIAZA-9-HYDROANTHRACENE AND METHOD FOR COLORING OF NATIVE OR SYNTHETIC MATERIALS

DESCRIPTION

The invention relates to novel derivatives of 9-oxo-1,9a,10-triaza-9-hydroanthracene, which are yellow- to violet-colored compounds having high color strength, to processes for their preparation and their use for the coloring of synthetic and natural materials, for example for pigmenting lacquer systems and plastics.

Colored derivatives derived from 9-oxo-1,9a,10-triaza-9-hydroanthracene of the formula A

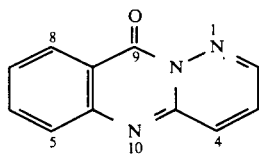

(A)

were described first in DYES AND PIGMENTS 7, 23 (1986):

Reaction of anthranilic acid B with acetic anhydride and reaction of the product thus obtained with hydrazine gives 3-amino-2-methyl-4-oxoquinazoline C:

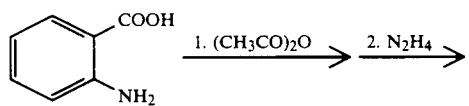

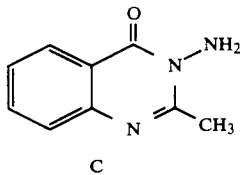

Reaction of compound C with acenaphthenequinone, phenanthrenequinone or isatin gives the polycycles D, E and F, which are yellow- to orange-colored compounds:

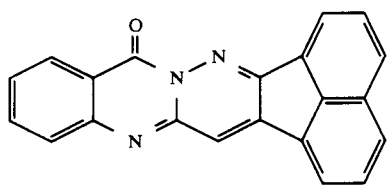

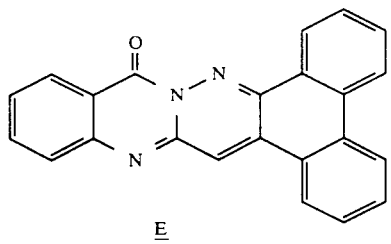

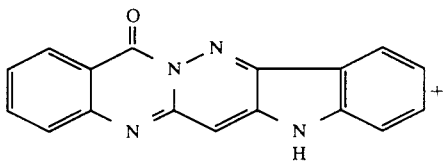

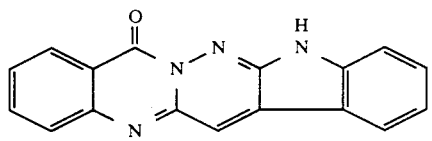

(isomeric with F)

The present invention relates to novel derivatives of 9-oxo-1,9a,10-triaza-9-hydroanthracenes of the general formula I

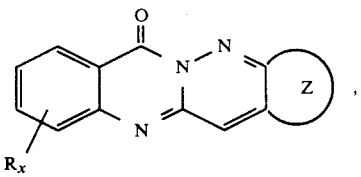

(I)

with the exception of the three compounds of the above-mentioned formulae D, E and F, in which (formula I) R denotes a hydrogen atom, halogen atom, preferably a chlorine or bromine atom, an alkyl-$C_1$–$C_4$, alkoxy-$C_1$–$C_4$ or denotes a trihalogenomethyl group, preferably a trifluoromethyl or trichloromethyl group, a —CO—$NH_2$—, —CO— NH-(alkyl-$C_1$–$C_4$) or —CO—N(alkyl-$C_1$–$C_4$)$_2$ group or a radical bound via the bridge member —S—, —SO— or —$SO_2$—, for example a phenyl, alkyl-$C_1$–$C_4$, —$NH_2$, —NH(alkyl-$C_1$–$C_4$), —N(alkyl-$C_1$–$C_4$)$_2$ or an alkylene-$C_1$–$C_4$—$OSO_3H$ group, or a fused-on 4- to 7-membered isocycle or heterocycle, for example from the series consisting of cyclobutane, cyclopentane, thiophene, pyrrole, furan, cyclohexane, pyridine, pyrimidine and cycloheptane, which itself can be part of a polycyclic system, for example from the series consisting of naphthalene, acenaphthene, phenanthrene and indole, x denotes an integer from 1 to 4, where for x>1 R can be identical or different, and Z denotes a fused-on 4- to 7-membered isocycle or heterocycle, for example from the series consisting of cyclobutane, cyclopentane, thiophene, pyrrole, furan, cyclohexane, pyridine, pyrimidine and cycloheptane, which itself can be part of a polycyclic system, for example from the series consisting of naphthalene, acenaphthene, phenanthrene and indole, in which each of the 4- to 7-membered isocycles or heterocycles mentioned and each of the polycyclic systems mentioned can be substituted by halogen atoms, alkyl-$C_1$-$C_4$, alkoxy-$C_1$-$C_4$, trihalogenomethyl, —CO—$NH_2$—, —CO—NH(alkyl-$C_1$-$C_4$) or —CO—N(alkyl—$C_1$-$C_4$)$_2$ groups or by phenyl, alkyl-$C_1$-$C_4$, —$NH_2$, —NH(alkyl-$C_1$-$C_4$), —N(alkyl-$C_1$-$C_4$)$_2$ or alkylene-$C_1$-$C_4$—$OSO_3H$ groups which are bound via the bridge member —S—, —SO— or —$SO_2$—.

The present invention also relates to a process for the preparation of the novel compounds of the general formula I mentioned by reacting anthranilic acid derivatives of the general formula II

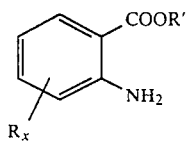

(II)

in which R' represents a hydrogen atom or an alkyl-$C_1$-$C_4$ or aryl group, for example a phenyl or toluyl group, R and x have the abovementioned meanings first with 1 to about 50 mol, preferably about 4 to about 15 mol, of acetic anhydride at temperatures of about 50 to about 180° C., if necessary at elevated or reduced pressure, preferably at the boiling temperature of acetic anhydride under standard conditions, in which the acetic anhydride at the same time serves as the reaction medium, then reacting the product with 1 to about 10 mol, preferably about 2 to about 6 mol, of hydrazine at temperatures of about 0° to about 120° C., if necessary at elevated or reduced pressure, preferably at about 15° to about 70° C. at atmospheric pressure, subsequently reacting the reaction product obtained of the general formula III

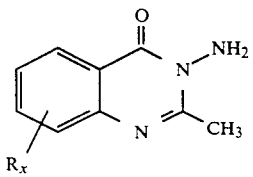

(III)

in which R and x have the abovementioned meanings with 1 to about 2 mol, preferably about 1.1 to about 1.2 mol, of the diketone of the general formula IV

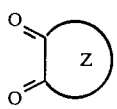

(IV)

in which Z has the abovementioned meaning at temperatures of about 140° to about 240° C., preferably about 160° to about 180° C., in an organic solvent which is inert towards the reactants, if necessary at elevated or reduced pressure, while simultaneously removing the water formed in the reaction.

The organic solvents which are used in the last step and are inert towards the reactants can be, for example, substituted or unsubstituted aliphatic or aromatic hydrocarbons, ethers, amides or mixtures thereof, preferably o-dichlorobenzene, diisopropylnaphthalene (mixture of isomers), 1-chloronaphthalene or a mixture consisting of 76.5% of diphenyl ether and 23.5% of diphenyl (®Dowtherm A).

The reaction with hydrazine to be carried out in the second step can also take place in an alcoholic medium, for example in methanol or ethanol.

In the reaction of the anthranilic acid derivatives of the general formula II with acetic anhydride which takes place in the first step, a molar ratio of 1:1 is in principle sufficient. However, since excess acetic anhydride expediently serves as the reaction medium, it is recommended to use acetic anhydride in a more or less large molar excess, for example in a molar ratio of 1:1 to 1: about 50.

The compounds of the general formula I obtained in accordance with the process are, depending on the type of substitution, yellow- to violet-colored, mostly slightly soluble compounds having a high color strength and are suitable for the coloring of synthetic and natural materials, for example for pigmenting lacquer systems and plastics.

The compounds of the formula I are obtained in the synthesis in a high-boiling solvent in highly crystalline form and are in this form in general not suitable for coloring various materials. First they have to be converted into a more finely divided form by suitable measures. These measures can be, for example, millings or also reprecipitations, in which the compound is dissolved in a suitable medium and reprecipitated. Apart from polyphosphoric acid and trifluoroacetic acid, in particular 96 to 100% strength sulfuric acid is suitable for this reprecipitation. The resulting solution is then hydrolyzed by pouring it into water. This gives very finely divided particles, which have a high color strength when pigmenting, for example, acrylic melamine lacquer system or polyolefins. When this aftertreatment of the compounds obtained of the general formula I is carried out, it is found, after X-ray diffraction diagrams are recorded, that a compound can be present in different crystalline modifications.

Depending on the particular use, the pigments which are obtained after hydrolysis can be brought into a form which has higher hiding power by heating them immediately after hydrolysis in the medium obtained (for example in sulfuric acid medium diluted with water) to temperatures of 60° to 100° C. However, it is also possible first to isolate the finely divided pigment and then to heat it in aqueous medium with the addition of an organic solvent, such as, for example, an alcohol, for example ethanol or isobutanol, or an aromatic compound, such as, for example, toluene, or a carboxamide, such as, for example, dimethylformamide, if necessary under pressure, to temperatures of about 80° to about 150° C.

It is also possible to convert the pigments according to the invention of the general formula I by milling into a form suitable for use. These millings can be carried out in the presence of water and/or an organic solvent as described above. The millings can also be carried out in the presence of an inorganic salt as milling auxiliary, such as, for example, sodium sulfate or sodium chloride, or even without any milling auxiliary.

In these operations, the properties of these novel colorants with regard to their practical application can be considerably improved by the addition of a surface-active compound.

The methods for obtaining certain crystalline properties, such as, for example, specific surface area, particle size distribution, particle form are highly dependent on the type and number of the substituents present in the colorants according to the invention.

Furthermore, to improve certain coloristic or fastness properties, it may be advantageous to prepare mixtures of the compounds of the general formula I. In the simplest case, this can be achieved by mixing two or more compounds of the general formula I by mechanical means; this operation in general serves to establish a certain shade.

However, it is also possible to prepare so-called mixed crystals. A mixed crystal or a solid solution is present if one or more compounds are incorporated in the crystal lattice of a "host compound". The X-ray diffraction diagram of this mixed crystal then only shows the reflections of the "host compound", while the X-ray diffraction diagram of the corresponding mechanical mixture shows the reflections of all compounds involved. This type of procedure is chosen if it is desired to influence not only the coloristic but also the rheological and fastness properties.

The preparation of mixed crystals in the case of the compounds of the general formula I can be carried out by different methods:

On the one hand, two or several compounds of the general formula I, can be dissolved, for example, in 96 to 100% strength sulfuric acid and the resulting solution hydrolyzed by pouring it into water. On the other, a mixture consisting of two or more 3-amino-2-methyl-4-oxoquinazolines (cf. the abovementioned general formula III) can be reacted with a 1,2-diketone.

Materials which can be colored or pigmented with the compounds of the general formula I are, for example, natural resins or synthetic resins, such as polymerization or polycondensation resins, but also cellulose ethers or cellulose esters.

EXPERIMENTAL PART

General procedure for the preparation of 3-amino-2-methyl-4-oxoquinazolines of the general formula III:

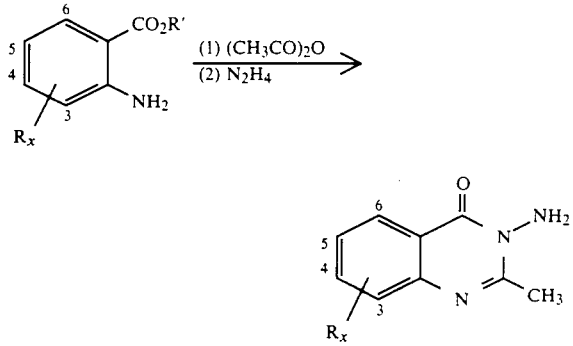

a parts of the anthranilic acid derivative are heated to boiling in b parts of acetic anhydride for 3 to 5 hours. The solvent is then removed, and the residue is dried in a desiccator over potassium hydroxide. The substance thus obtained is stirred with c ml of methanol, and with cooling d parts of hydrazine hydrate are added dropwise at 10° to 15° C. The temperature is then maintained at 20° C. for 30 minutes, at 40° C. for 30 minutes and at the boiling temperature for 30 minutes. The product is then filtered off with suction at 20° C., the residue is washed with a small amount of methanol and dried at 60° C. in a circulating air cabinet. This gives X parts of 3-amino-2-methyl-4-oxoquinazoline (y% of theory, relative to the anthranilic acid derivative), which can be used without further purification for the reaction with the 1,2-diketones.

| Experiment | R | R' | a | b | c | d | X | y % | | R |
|---|---|---|---|---|---|---|---|---|---|---|
| 1 | 5-Cl | H | 85.8 | 300 | 300 | 125 | 66.7 | 64 | 1 | 5-Cl |
| 2 | 4-Cl | CH$_3$ | 92.8 | 300 | 150 | 125 | 95.7 | 91 | 2 | 4-Cl |
| 3 | 3,5-Cl$_2$ | H | 80.0 | 240 | 300 | 125 | 91.4 | 95 | 3 | 3,5-Cl$_2$ |
| 4 | 3,4,5-Cl$_3$ | H | 120.3 | 300 | 1200 | 125 | 123.9 | 89 | 4 | 3,4,5-Cl$_3$ |
| 5 | 4-CF$_3$ | H | 102.5 | 300 | 500 | 125 | 73.3 | 60 | 5 | 4-CF$_3$ |
| 6 | 5-Br | H | 22.3 | 60 | 60 | 25 | 10.2 | 40 | 6 | 5-Br |
| 7 | 3,5-Br$_2$ | CH$_3$ | 94.6 | 200 | 180 | 75 | 91.5 | 92 | 7 | 3,5-Br$_2$ |
| 8 | 6-CH$_3$ | H | 22.9 | 90 | 90 | 38 | 22.4 | 79 | 8 | 6-CH$_3$ |
| 9 | 5-CH$_3$ | H | 75.6 | 300 | 300 | 125 | 82.7 | 88 | 9 | 5-CH$_3$ |
| 10 | 3-CH$_3$ | H | 22.9 | 90 | 90 | 38 | 24.4 | 86 | 10 | 3-CH$_3$ |
| 11a | H | C$_2$H$_5$ | 82.6 | 300 | 300 | 125 | 70.5 | 80 | 11 | |
| 11b | H | CH$_3$ | 75.6 | 300 | 300 | 125 | 60.5 | 69 | 11 | |
| 12 | (cyclohexadiene-5,4) | H | 18.7 | 100 | 100 | 25 | 21.5 | 96 | 12 | (cyclohexadiene-5,4) |

The examples which follow serve to illustrate the invention without limiting it thereto.

The parts and percentages listed in the examples which follow are by weight.

General procedure for the preparation of 9-oxo-1,9a,10-triaza-9-hydroanthracenes:

a parts of the particular 3-amino-2-methyl-4-oxoquinazoline 1–12, which has been prepared as described above, are heated with b parts of 1,2-diketone in c parts of solvent for d hours at a temperature of T° C. in a water separator The product is filtered off with suction at 80 to 100° C., washed with warm solvent, the filter cake is stirred in dichloromethane, the solid is again filtered off with suction, washed with dichloromethane and dried (60° C., circulating air cabinet) to give x parts (y% of theory) of the 9-oxo-1,9a,10-triaza-9-hydroanthracene derivative. m parts of the product thus obtained are dissolved or suspended at 15° to 20° C. in n parts of 96 to 100% strength sulfuric acid and maintained at this temperature for 1 hour. The mixture is poured into o parts of ice water, the mixture is then heated at 90° C. for 2 hours, the product is filtered off with suction, washed until neutral, dried, and p parts (q%) of the 9-oxo-1,9a,10-triaza-9-hydroanthracene derivative are recovered.

Abbreviations for the 1,2-diketones and solvents used in the table below

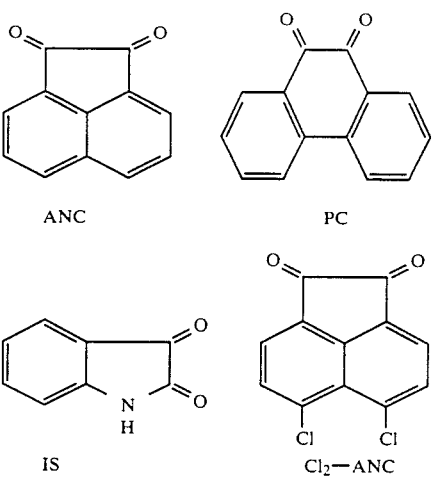

ANC = acenaphthenequinone
PC = phenanthrenequinone
IS = isatin
o-DCB = 1,2-dichlorobenzene
DT = Dowtherm A = 76.5% of diphenyl ether, 23.5% of diphenyl
DIN = diisopropylnaphthalene (mixture of isomers)
CN = 1-chloronaphthalene

| Experiment | a | R | | b | 1,2-diketone | c | solvent | d | T °C. | X | y % | Product | m | n | o | p | q % |
|---|---|---|---|---|---|---|---|---|---|---|---|---|---|---|---|---|---|
| 13 | 20.9 | 5-Cl | 1 | 20.0 | ANC | 500 | o-DCB | 6 | reflux | 32.7 | 92 | 13 | 30.0 | 300 | 2400 | 29.9 | 99 |
| 14 | 20.9 | 5-Cl | 1 | 22.9 | PC | 500 | o-DCB | 6 | reflux | 29.8 | 78 | 14 | 25.0 | 250 | 2800 | 24.3 | 97 |
| 15 | 20.9 | 4-Cl | 2 | 20.9 | ANC | 500 | o-DCB | 6 | reflux | 27.7 | 78 | 15 | 25.0 | 250 | 2000 | 23.7 | 96 |
| 16 | 20.9 | 4-Cl | 2 | 22.9 | PC | 500 | o-DCB | 6 | reflux | 24.8 | 65 | 16 | 24.0 | 250 | 2000 | 23.7 | 96 |
| 17 | 20.9 | 4-Cl | 2 | 16.2 | IS | 500 | o-DCB | 6 | reflux | 6.0 | 19 | 17 | 5.5 | 100 | 800 | 5.0 | 91 |
| 18 | 24.4 | 3,5-Cl$_2$ | 3 | 20.0 | ANC | 500 | o-DCB | 6 | reflux | 31.2 | 80 | 18 | 28.0 | 280 | 2800 | 24.1 | 86 |
| 19 | 24.4 | 3,5-Cl$_2$ | 3 | 22.9 | PC | 500 | o-DCB | 6 | reflux | 28.2 | 68 | 19 | 25.0 | 250 | 2500 | 16.7 | 67 |
| 20 | 24.4 | 3,5-Cl$_2$ | 3 | 16.2 | IS | 500 | o-DCB | 6 | reflux | 4.2 | 12 | 20 | 3.5 | 150 | 1500 | 2.4 | 69 |
| 21 | 27.8 | 3,4,5-Cl$_3$ | 4 | 20.0 | ANC | 500 | o-DCB | 7 | reflux | 30.2 | 71 | 21 | 27.7 | 380 | 3000 | 27.4 | 99 |
| 22 | 27.8 | 3,4,5-Cl$_3$ | 4 | 22.9 | PC | 500 | o-DCB | 7 | reflux | 35.6 | 79 | 22 | 34.0 | 640 | 5000 | 32.0 | 94 |
| 23 | 24.3 | 4-CF$_3$ | 5 | 20.0 | ANC | 500 | o-DCB | 10 | reflux | 29.8 | 77 | 23 | 28.4 | 300 | 2400 | 27.3 | 96 |
| 24 | 24.3 | 4-CF$_3$ | 5 | 22.9 | PC | 500 | o-DCB | 10 | reflux | 14.8 | 36 | 24 | 13.7 | 150 | 1200 | 12.4 | 91 |
| 25 | 8.46 | 5-Br | 6 | 6.70 | ANC | 170 | o-DCB | 10 | reflux | 10.6 | 80 | 25 | 10.6 | 150 | 1200 | 10.2 | 96 |
| 26 | 16.6 | 3,5-Br$_2$ | 7 | 10.0 | ANC | 250 | o-DCB | 7 | reflux | 17.9 | 75 | 26 | 17.6 | 200 | 1600 | 17.4 | 99 |
| 27 | 16.6 | 3,5-Br$_2$ | 7 | 11.4 | PC | 250 | o-DCB | 7 | reflux | 17.6 | 70 | 27 | 17.6 | 300 | 2600 | 17.2 | 98 |
| 28 | 9.45 | 6-CH$_3$ | 8 | 10.0 | ANC | 250 | o-DCB | 10 | reflux | 5.4 | 32 | 28 | 5.4 | 100 | 800 | 5.1 | 94 |
| 29 | 9.45 | 6-CH$_3$ | 8 | 11.4 | PC | 250 | o-DCB | 10 | reflux | 8.7 | 48 | 29 | 8.4 | 150 | 1200 | 8.0 | 95 |
| 30 | 18.9 | 5-CH$_3$ | 9 | 20.0 | ANC | 500 | o-DCB | 6 | reflux | 27.1 | 81 | 30 | 25.0 | 250 | 2500 | 24.4 | 98 |
| 31 | 18.9 | 5-CH$_3$ | 9 | 22.9 | PC | 500 | o-DCB | 6 | reflux | 20.7 | 57 | 31 | 18.0 | 280 | 2800 | 17.7 | 98 |
| 32 | 9.5 | 3-CH$_3$ | 10 | 10.0 | ANC | 250 | o-DCB | 6 | reflux | 14.2 | 85 | 32 | 13.5 | 200 | 1600 | 13.2 | 98 |
| 33 | 14.3 | 3-CH$_3$ | 10 | 11.5 | PC | 250 | o-DCB | 6 | reflux | 7.7 | 43 | 33 | 7.2 | 150 | 1200 | 6.5 | 90 |
| 34 | 17.8 | H | 11 | 19.3 | ANC | 300 | o-DCB | 4 | reflux | 29.2 | 89 | 34 | 10.0 | 120 | 900 | 9.8 | 98 |
| 35a | 8.75 | H | 11 | 11.4 | PC | 250 | DT | 6 | 170 | 10.0 | 81 | 35 | 8.0 | 150 | 1200 | 7.6 | 95 |
| 35b | 8.75 | H | 11 | 11.4 | PC | 250 | DIN | 6 | 170 | 11.0 | 89 | 35 | 8.0 | 150 | 1200 | 7.4 | 93 |
| 35c | 8.75 | H | 11 | 11.4 | PC | 250 | CN | 6 | 170 | 9.0 | 73 | 35 | 8.0 | 150 | 1200 | 7.6 | 95 |
| 36 | 6.92 | H | 11 | 10.5 | Cl$_2$—ANC | 200 | o-DCB | 6 | reflux | 7.6 | 49 | 36 | 6.9 | 150 | 1200 | 6.1 | 88 |
| 37 | 22.5 | 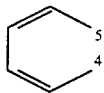 | 12 | 20.0 | ANC | 500 | o-DCB | 6 | reflux | 27.2 | 73 | 37 | 25.0 | 250 | 2000 | 23.7 | 95 |

-continued

| | | |
|---|---|---|
| 13 | 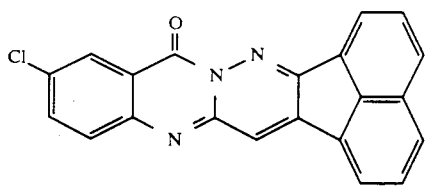 | C$_{21}$H$_{10}$N$_3$OCl<br>found C 70.0% H 2.7% N 11.6<br>yellow |
| 14 | 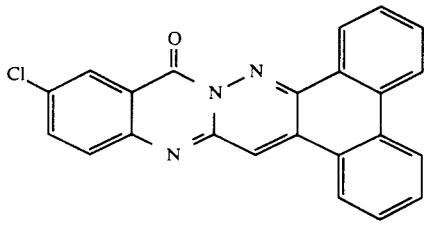 | C$_{23}$H$_{12}$N$_3$OCl<br>found C 70.1% H 3.1% N 10.8<br>orange |
| 15 | 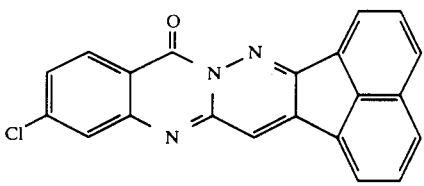 | C$_{21}$H$_{10}$N$_3$OCl<br>found C 71.4% H 2.8% N 11.9<br>greenish yellow |
| 16 | 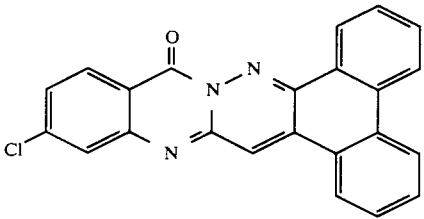 | C$_{23}$H$_{12}$N$_3$OCl<br>found C 72.3% H 3.0% N 11.1%<br>Cl 9.2%<br>orange |
| 17 | 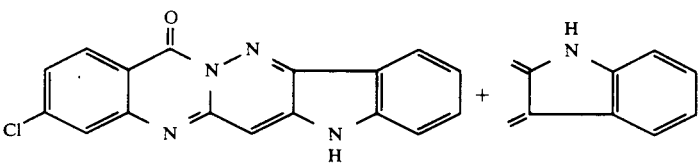 | C$_{17}$H$_9$N$_4$OCl<br>found C 60.8% H 2.8% N 16.8%<br>Cl 10.5%<br>orange |
| 18 | 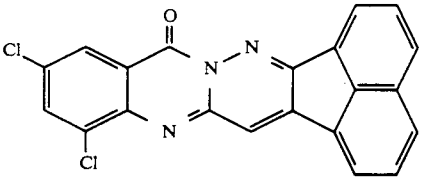 | C$_{21}$H$_9$N$_3$OCl$_2$<br>found C 64.8% H 2.3% N 10.8%<br>yellow |
| 19 | 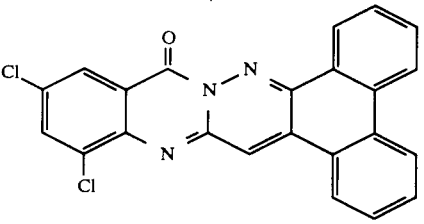 | C$_{23}$H$_{11}$N$_3$OCl$_2$<br>found C 66.1% H 2.7% N 10.0%<br>orange |
| 20 | 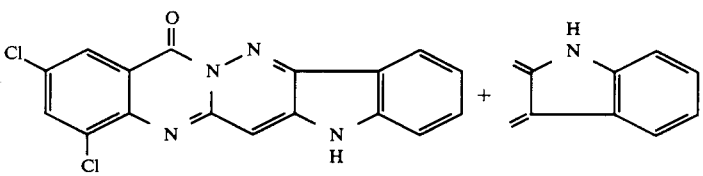 | C$_{17}$H$_8$N$_4$OCl$_2$<br>found C 55.2% H 2.1% N 13.8%<br>brown-orange |

-continued
| 21 | 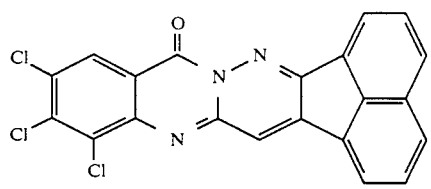 | $C_{21}H_8N_3OCl_3$<br>found C 59.5% H 1.7% N 9.4%<br>Cl 25.0%<br>yellow |
| --- | --- | --- |
| 22 | 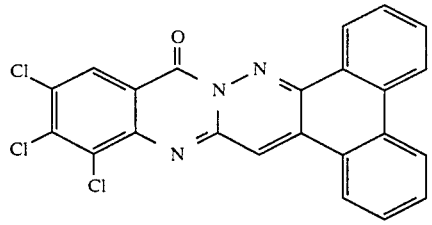 | $C_{23}H_{10}N_3OCl_3$<br>found C 61.4% H 2.3% N 8.7%<br>Cl 23.6%<br>orange |
| 23 | 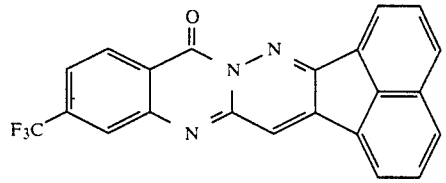 | $C_{22}H_{10}N_3OF_3$<br>found C 67.9% H 2.6% N 10.8%<br>greenish yellow |
| 24 | 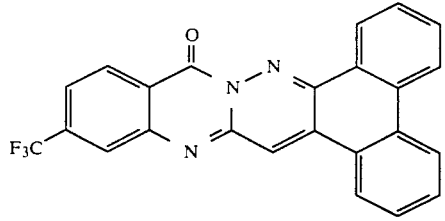 | $C_{24}H_{12}N_3OF_3$<br>found C 69.0% H 2.9% N 9.6%<br>orange |
| 25 | 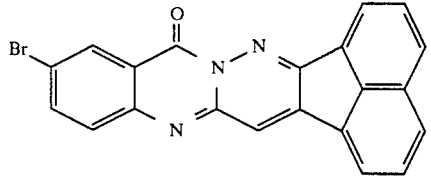 | $C_{21}H_{10}N_3OBr$<br>found C 64.0% H 2.8% N 9.9%<br>yellow |
| 26 | 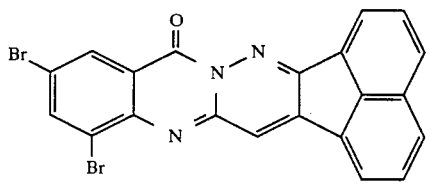 | $C_{21}H_9N_3OBr_2$<br>found C 53.0% H 1.9% N 8.8%<br>yellow |
| 27 | 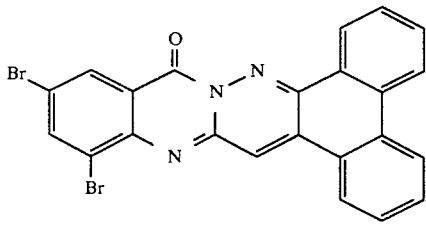 | $C_{23}H_{11}N_3OBr_2$<br>found C 54.4% H 2.1% N 8.8%<br>Br 31.9%<br>orange |

-continued
| 28 | 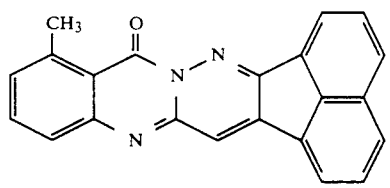 | C₂₂H₁₃N₃O found C 78.1% H 3.8% N 12.5% yellow |
| --- | --- | --- |
| 29 | 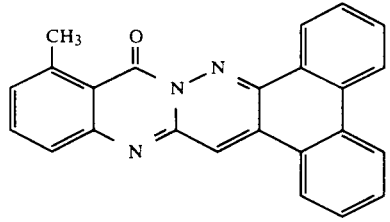 | C₂₄H₁₅N₃O found C 77.6% H 3.8% N 12.0% orange |
| 30 | 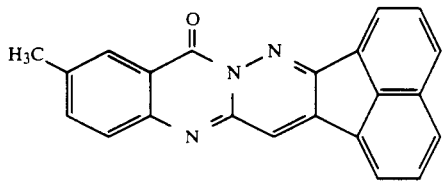 | C₂₂H₁₃N₃O found C 74.6% H 3.7% N 11.7% yellow |
| 31 | 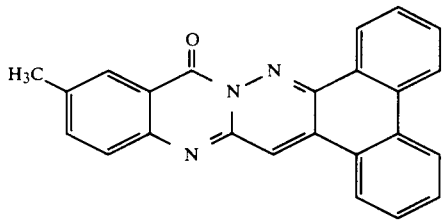 | C₂₄H₁₅N₃O found C 79.1% H 4.1% N 10.7% orange |
| 32 | 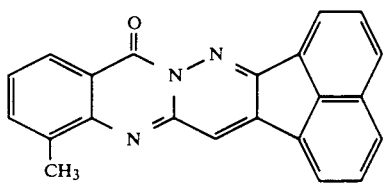 | C₂₂H₁₃N₃O found C 78.2% H 3.8% N 12.5% yellow |
| 33 | 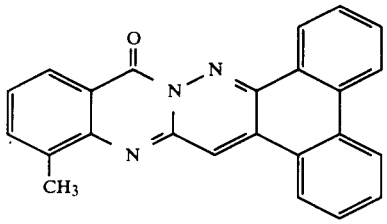 | C₂₄H₁₅N found C 78.1% H 4.2% N 11.3% orange |
| 34 | 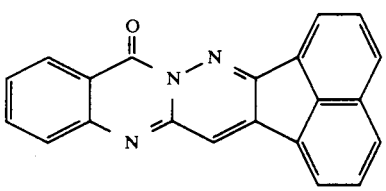 | yellow |

| | |
|---|---|
| 35 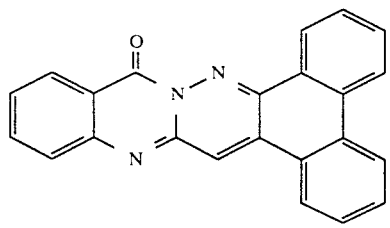 | orange |
| 36 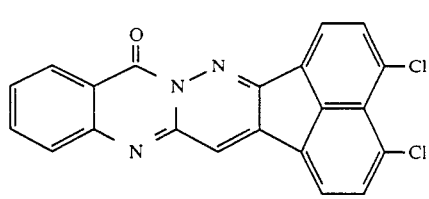 | $C_{21}H_9N_3OCl_2$<br>found C 64.2% H 2.4% N 10.5%<br>Cl 18.3%<br>yellow |
| 37 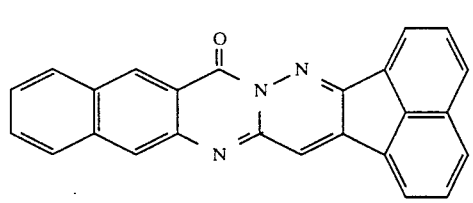 | $C_{25}H_{13}N_3O$<br>found C 79.2% H 3.5% N 11.2%<br>orange |

The structure of compounds 13 to 37 listed above is further confirmed by $^1$H-NMR spectroscopy.

EXPERIMENT 38

14.2 parts of I (R=5-cl) 13 and 3.2 parts of I (R=H) 34 are dissolved at 20° C. in 250 parts of 96% strength sulfuric acid. The solution obtained is run into 2500 parts of water at 0° C. The resulting suspension is then heated at 90° C. for 2 hours. The product is then filtered off with suction, washed until neutral and dried. This gives 8.5 parts (98% of theory) of a yellow pigment whose X-ray diffraction diagram only shows the reflections of compound 13.

EXPERIMENT 39

9.76 parts of 3 and 2.09 parts of 1 and also 10.1 parts of acenaphthenequinone are heated to boiling in 300 ml of o-dichlorobenzene in a water separator for 7 hours. The product is then filtered off with suction at 80° C., washed with warm o-dichlorobenzene, the residue is stirred in dichloromethane, filtered off with suction, and dried to give 16.5 parts (86% of theory) of a mixed crystal, which in an X-ray diffraction diagram only shows the reflections of compound 18.

EXAMPLE 40

The pigments obtained are compared to one another after incorporation into a TSA lacquer system.

a) 30.0 parts of compound 18 are dissolved in 400 parts of 100% strength sulfuric acid at 10° to 15° C., and this solution is hydrolyzed by pouring it into 3200 parts of water at 0° C. The resulting suspension is additionally heated at 90° C. for 2 hours, the product is filtered off with suction, washed until neutral and dried. 29.3 parts (98% of theory) of 18 are recovered as a yellow pigment.

15.0 parts of compound 18, such as was obtained by experiment 18, are milled in a stirred ball mill with 140 parts of water and 10 parts of isobutanol in the presence of glass beads (2 mm in diameter) at room temperature for 3 hours. The alcohol is distilled off with steam, and the remaining suspension is filtered off with suction, and the residue is washed and dried. 15.0 parts of a yellow pigment are recovered, which in its coloristic properties is comparable to the pigment obtained according to a).

15.0 parts of compound 18, such as was obtained by experiment 18, are milled in a roll mill with 30 parts of sodium sulfate in the presence of porcelain balls for 4 hours. The mill base is treated with 600 parts of water, and the residue is filtered off with suction, washed until salt-free and dried. This gives 29.2 parts (98% of theory) of a yellow pigment, which is clearly more transparent than the one obtained according to a).

We claim:

1. A derivative of 9-oxo-1, 9a,10-triaza-9-hydroanthracene of the formula I

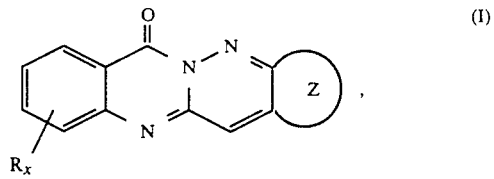 (I)

with the exception of the three compounds of the formulae

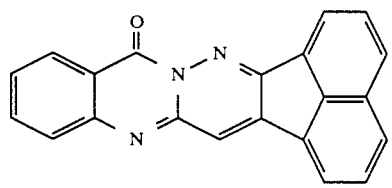

D

-continued

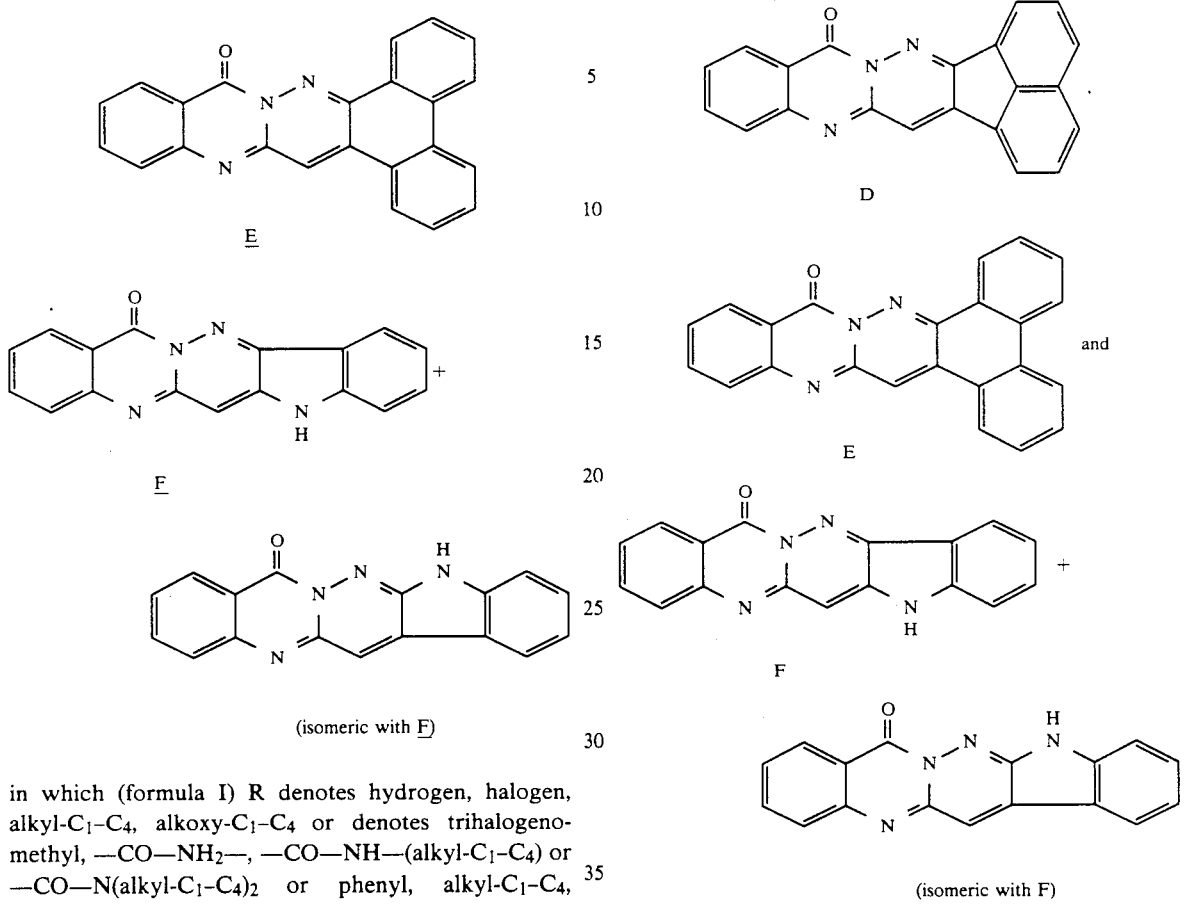

in which (formula I) R denotes hydrogen, halogen, alkyl-$C_1$–$C_4$, alkoxy-$C_1$–$C_4$ or denotes trihalogenomethyl, —CO—$NH_2$—, —CO—NH—(alkyl-$C_1$–$C_4$) or —CO—N(alkyl-$C_1$–$C_4$)$_2$ or phenyl, alkyl-$C_1$–$C_4$, —$NH_2$, —NH(alkyl-$C_1$–$C_4$), —N(alkyl-$C_1$–$C_4$)$_2$ or alkylene-$C_1$–$C_4$—$OSO_3H$ bound via the bridge member —S—, —SO— or —$SO_2$—, or a fused-on 4- to 7-membered isocyclic or heterocyclic aliphatic or aromatic, x denotes an integer from 1 to 4, where from x>1 R is identical or different, and Z denotes a fused-on 4- to 7-membered isocyclic or heterocyclic aliphatic or aromatic, wherein the cyclic moieties are unsubstituted or substituted by halogen, alkoxy-$C_1$–$C_4$, trihalogenomethyl, —CO—$NH_2$—, —CO—NH(alkyl-$C_1$–$C_4$) or —CO—N(alkyl-$C_1$–$C_4$)$_2$ or by phenyl, alkyl-$C_1$–$C_4$, —$NH_2$, NH(alkyl-$C_1$–$C_4$), —N(alkyl-$C_1$–$C_4$)$_2$ or alkylene-$C_1$–$C_4$—$OSO_3H$ which are bound via the bridge member —S—, —SO— or —$SO_2$—, with the proviso that if R is hydrogen, then Z is substituted by one or more of said substituents.

2. A derivative of 9-oxo-1,9a,10-triaza-9-hydroanthracene of the formula I

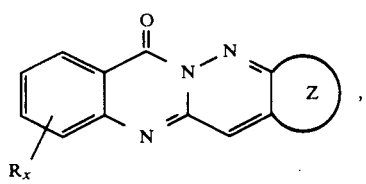

with the exception of the three compounds of the formulae in which (formula I) R denotes hydrogen, chlorine or bromine, alkyl-$C_1$–$C_4$, alkoxy-$C_1$–$C_4$, trifluoromethyl or trichloromethyl, —CO—$NH_2$—, —CO—NH— (alkyl-$C_1$–$C_4$) or —CO—N(alkyl-$C_1$–$C_4$)$_2$ or phenyl, alkyl-$C_1$–$C_4$, —$NH_2$, —NH(alkyl-$C_1$–$C_4$), —N(alkyl-$C_1$–$C_4$)$_2$ or alkylene-$C_1$–$C_4$—$OSO_3H$, bound via the bridge member, —S—, —SO— or —$SO_2$—, or a fused-on 4- to 7-membered isocyclic or heterocyclic aliphatic or aromatic from the group consisting of cyclopentane, cyclohexane, cyclopentane, thiophene, pyrrole, furan, cyclohexane, pyridine, pyrimidine, cycloheptane, naphthalene, acenaphthene, phenanthrene and indole, x denotes an integer form 1 to 4, where for x>1 R is identical or different, and Z denotes a fused-on 4- to 7-membered isocyclic or heterocyclic aliphatic or aromatic from the group consisting of cyclobutane, cyclopentane, thiophene, pyrrole, furan, cyclohexane, pyridine, pyrimidine, cycloheptane, naphthalene, acenaphthene, phenanthrene and indole, wherein the cyclic moieties are unsubstituted or substituted by chlorine or bromine, alkoxy-$C_1$–$C_4$, trifluoromethyl, trichloromethyl, —CO— $NH_2$—, —CO—NH(alkyl-$C_1$–$C_4$) or —CO—N(alkyl-$C_1$–$C_4$)$_2$ or by phenyl, alkyl-$C_1$–$C_4$, —$NH_2$, —NH(alkyl-$C_1$–$C_4$), —N(alkyl-$C_1$–$C_4$)$_2$ or alkylene-$C_1$–$C_4$—$OSO_3H$ which are bound via the bridge member —S—, —SO— or —$SO_2$—, with the proviso that if R is hydrogen, then Z is substituted by one or more of said substituents.

3. A mixed crystal consisting of at least two compounds of the formula I mentioned in claim 1, wherein at least one of these compounds is present in the crystal lattice of one of the other compounds.

* * * * *